(12) United States Patent
Ellman

(10) Patent No.: US 8,063,030 B2
(45) Date of Patent: Nov. 22, 2011

(54) EXTENDED CYCLE MULTIPHASIC ORAL CONTRACEPTIVE METHOD

(75) Inventor: Herman Ellman, Boonton Township, NJ (US)

(73) Assignee: Warner Chilcott Company, LLC, Fajardo, PR (US)

( * ) Notice: Subject to any disclaimer, the term of this patent is extended or adjusted under 35 U.S.C. 154(b) by 661 days.

(21) Appl. No.: 11/704,307

(22) Filed: Feb. 9, 2007

(65) Prior Publication Data

US 2007/0207945 A1 Sep. 6, 2007

Related U.S. Application Data

(60) Provisional application No. 60/792,653, filed on Apr. 18, 2006, provisional application No. 60/778,067, filed on Mar. 2, 2006.

(51) Int. Cl.
*A61K 31/56* (2006.01)
(52) U.S. Cl. .................................. 514/170; 514/182
(58) Field of Classification Search .................. 514/170, 514/182
See application file for complete search history.

(56) References Cited

U.S. PATENT DOCUMENTS

| | | | |
|---|---|---|---|
| 4,962,098 A | 10/1990 | Boissonneault | 514/170 |
| 5,010,070 A * | 4/1991 | Boissonneault | 514/171 |
| RE35,724 E * | 2/1998 | Pasquale | 514/170 |
| 5,756,490 A * | 5/1998 | Lachnit et al. | 514/170 |
| 5,898,032 A | 4/1999 | Hodgen | 514/178 |
| 6,027,749 A | 2/2000 | Schmidt-Gollwitzer et al. | 424/464 |
| 6,251,956 B1 * | 6/2001 | Kafrissen et al. | 514/171 |
| 6,312,722 B1 | 11/2001 | Schmidt-Gollwitzer et al. | 424/464 |
| 6,500,814 B1 | 12/2002 | Hesch | 514/170 |
| 6,797,282 B2 | 9/2004 | Kafrissen et al. | 424/464 |
| 2001/0020015 A1 | 9/2001 | Kafrissen et al. | 514/171 |
| 2003/0139381 A1 | 7/2003 | Bell et al. | 514/170 |
| 2003/0219471 A1 | 11/2003 | Caubel et al. | 424/449 |
| 2003/0225048 A1 | 12/2003 | Caubel et al. | 514/170 |
| 2004/0142914 A1 | 7/2004 | Friedman et al. | 514/170 |
| 2004/0202713 A1 | 10/2004 | Van Beek et al. | 424/464 |
| 2004/0220152 A1 | 11/2004 | Ben-Maimon et al. | 514/170 |
| 2005/0064031 A1 | 3/2005 | Stockemann et al. | 424/464 |
| 2005/0090475 A1 | 4/2005 | LaGuardia | 514/170 |
| 2005/0113350 A1 | 5/2005 | Duesterberg et al. | 514/170 |
| 2005/0143359 A1 | 6/2005 | Bell et al. | 514/170 |
| 2007/0259840 A1 | 11/2007 | Endrikat et al. | |

FOREIGN PATENT DOCUMENTS

| | | |
|---|---|---|
| DE | 4313926 | 11/1994 |
| EP | 0770388 | 5/1997 |
| WO | 98/04268 | 2/1998 |
| WO | 2005/049142 | 6/2005 |
| WO | 2005/092441 | 10/2005 |
| WO | 2005/102247 | 11/2005 |
| WO | 2007/002910 | 1/2007 |

OTHER PUBLICATIONS

Wiegratz and Kuhl, Drugs, 2004;64(21):2447-2462.*
Edwards, L.A., "An Update on Oral Contraceptive Options", Formulary, Advanstar Communications, Cleveland, OH, vol. 39, No. 2, Feb. 2004, pp. 104-121.
Foidart, Jean-Michel, et al. "The use of an oral contraceptive containing ethinylestradiol and drospirenone in an extended regimen over 126 days," Contraception 73 (2006) 34-40.

* cited by examiner

*Primary Examiner* — San-Ming Hui
(74) *Attorney, Agent, or Firm* — Fitzpatrick, Cella, Harper & Scinto

(57) ABSTRACT

A multiphasic method of contraception comprising the steps of sequentially administering to a female of child bearing age a Phase I composition containing a progestogen in an amount equivalent to about 0.3 to about 1.5 mg norethindrone acetate and an estrogen in an amount equivalent to about 5 to about 15 mcg of ethinyl estradiol for about 7 to about 14 days; a Phase II composition containing a progestogen in an amount equivalent to about 0.3 to about 1.5 mg of norethindrone acetate and an estrogen in an amount equivalent to about 10 to about 25 mcg of ethinyl estradiol for about 14 to about 22 days; a Phase III composition containing a progestogen in an amount equivalent to about 0.3 to about 1.5 mg of norethindrone acetate and an estrogen in an amount equivalent to about 15 to about 35 mcg of ethinyl estradiol for about 20 to about 31 days; and an optional Phase IV composition containing (i) an estrogen in an amount equivalent to about 5 to about 20 mcg of ethinyl estradiol, or (ii) a placebo or a non-steroidal component, or (iii) a combination of (i) and (ii), for about 2 to about 8 days. The ethinyl estradiol equivalent amount of estrogen in each of the successive Phases II and III is at least 5 mcg greater than the ethinyl estradiol equivalent amount of estrogen in the immediately-preceding phase.

25 Claims, No Drawings

EXTENDED CYCLE MULTIPHASIC ORAL CONTRACEPTIVE METHOD

This application claims the benefit of U.S. provisional application No. 60/792,653, filed Apr. 18, 2006 and U.S. provisional application No. 60/778,067, filed Mar. 2, 2006. The entire disclosure of both provisional applications are incorporated by reference herein.

BACKGROUND OF THE INVENTION

1. Field of the Invention

This invention is directed to a multiphasic estrogenic/progestogenic contraceptive regimen that may be used for an extended period of time. In the multiphasic regimen of the present invention, the amount of estrogen administered in each successive phase of the first three phases is greater than the amount of estrogen administered in the previous phase. The inventive regimen provides contraceptive efficacy and enables the user to maintain menstrual cycle control. A multiphase contraceptive kit that may be used to practice the method of this invention is also contemplated.

2. Related Background Art

Contraceptive compositions containing both estrogenic and progestogenic compounds are known to be highly effective in controlling ovulation and conception. The progestogenic component of the composition is primarily responsible for the contraceptive efficacy of the composition, while the estrogenic component is included to reduce undesired side effects, such as breakthrough bleeding or spotting. In fact, small amounts of estrogen help stabilize the endometrium and allow cyclic withdrawal bleeding, similar to the natural menstrual cycle.

The earliest of these estrogenic/progestogenic contraceptive compositions was administered monophasically (fixed dose) and contained a relatively high level of estrogenic component. To minimize estrogen's major negative side effect on blood clotting factors, the dose of estrogen was reduced over time. However, as estrogen doses decreased, the incidences of unwanted breakthrough bleeding or spotting have generally increased.

Multiphasic oral contraceptives were introduced to artificially simulate the natural rise of progesterone over the cycle in an attempt to solve this problem. A constant goal, however, has been to reduce the estrogenic potency of such compositions without reducing contraceptive efficacy and increasing undesired side effects.

In U.S. Pat. No. 5,888,543, various regimens are disclosed where a combination of progestin and estrogen are administered in a monophasic or multiphasic regimens (varied dose, e.g., biphasic or triphasic). In one embodiment, a combination of a progestin composition and an estrogen composition is administered such that the daily dosage of the second phase progestin is greater than the daily dosage of progestin in the first phase and the daily dosage of the second phase estrogen is greater than or equal to the daily dosage of estrogen in the first phase.

A particularly advantageous technique for reducing total estrogenic administration is described in U.S. Pat. No. 4,962,098. This describes a triphasic method of contraception using a progestogen/estrogen combination in which the amount of estrogen is increased stepwise over the three phases. The first phase is 4-7 days, the second phase is 5-8 days and the third phase is 7-12 days. Preferably, the administration of the contraceptive compositions for the three phases will be 21 days followed by a 7 day placebo period. For all three phases the progestogen is 0.5 to 1.5 mg of norethindrone acetate, while about 10 to 30 mcg of ethinyl estradiol is used in the first phase, about 20 to 40 mcg of ethinyl estradiol is used in the second phase and 30 to 50 mcg of ethinyl estradiol is employed in the third phase.

U.S. Pat. No. 5,010,070 is related to U.S. Pat. No. 4,962,098 and discloses a multiphasic contraceptive kit containing ethinyl estradiol and norethindrone acetate in first, second, and third phase compositions.

Recently, numerous oral contraceptive regimens extending treatment to three cycles have become known in the art. One such extended oral contraceptive regimen is disclosed in U.S. Pat. No. 5,898,032, where estrogen and progestin are administered in a combined dosage form, preferably monophasically, for 60 to 110 consecutive days, followed by an administration free period of 3 to 10 days. The amount of estrogen and progestin administered daily are equivalent to about 5-35 mcg of ethinyl estradiol and about 0.025 to 10 mg of norethindrone acetate, respectively. In one particular embodiment, the combined dosage form is administered for 84 days followed by 7 pill free days. Following this particular regimen is said to result in four treatments and menstrual cycles during the year.

Yet another extended oral contraceptive regimen is disclosed in U.S. Patent Application Publication No. 2005/0113350 A1, providing continuous hormonal treatment for a desired period of time longer than 21-28 days. Here, a first composition containing a progestin and estrogen is administered in the first 21-28 days, followed by a second composition of progestin and estrogen in an amount higher than the amount of the first composition, comprising a mono or multiphase sequence of dosages. The preferred regimen comprises dosages administered over an 84-112 day duration.

There are, however, disadvantages to using an extended monophasic oral contraceptive regimen. Typically, monophasic oral contraceptives administered for an extended period of time have poor initial cycle control.

Moreover, while perhaps reducing the number of periods to four per year, another drawback of conventional monophasic oral contraceptive regimens extended over three cycles is the excessive breakthrough bleeding that often results. Breakthrough bleeding, or spotting, is the undesired bleeding that sometimes occurs between regular withdrawal bleeding periods. It is believed that breakthrough bleeding is increasingly difficult to effectively suppress as durations of treatment extend beyond one month. With many three-cycle regimens, irregular bleeding occurs with increasing frequency as the treatment begins to break down until the oral contraceptive is withdrawn at the end of third cycle, finally resulting in the onset of the expected withdrawal bleeding. While excessive breakthrough bleeding may be diminished by using a higher dose of estrogen, this solution inevitably brings with it the risk of negative side effects of elevated estrogen on blood clotting factors. Finally, once breakthrough bleeding is under control, the user becomes functionally amenorrheic. Psychologically, this does not reassure the user that she is not pregnant.

Accordingly, there is presently a need for an extended oral contraceptive regimen that significantly reduces the occurrence of breakthrough bleeding commonly associated with three-month extended cycle regimens while at the same time only gradually increasing the dosage of estrogen delivered over the course of treatment.

SUMMARY OF THE INVENTION

The present invention is directed to a multiphasic method of contraception that provides for sequentially administering to a female of child bearing age (a) a Phase I composition containing a progestogen in an amount equivalent to about 0.3 to about 1.5 mg norethindrone acetate and an estrogen in an amount equivalent to about 5 to about 15 mcg of ethinyl estradiol for about 7 to about 14 days; (b) a Phase II composition containing a progestogen in an amount equivalent to about 0.3 to about 1.5 mg of norethindrone acetate and an estrogen in an amount equivalent to about 10 to about 25 mcg of ethinyl estradiol for about 14 to about 22 days; (c) a Phase III composition containing a progestogen in an amount equivalent to about 0.3 to about 1.5 mg of norethindrone acetate and an estrogen in an amount equivalent to about 15 to about 35 mcg of ethinyl estradiol for about 20 to about 31 days; and (d) an optional, but preferable, Phase IV composition containing (i) an estrogen in an amount equivalent to about 5 to about 20 mcg of ethinyl estradiol, or (ii) a placebo or a non-steroidal component, or (iii) a combination of (i) and (ii), for about 2 to about 8 days, wherein the ethinyl estradiol equivalent amount of estrogen in each of the successive Phases II and III is at least 5 mcg greater than the ethinyl estradiol equivalent amount of estrogen in the immediately-preceding phase.

In a particularly significant embodiment of the invention, the sequential administration of the Phase I, II, III, and IV compositions is continued through the completion of the administration of the Phase IV composition, to provide an extended cycle multiphasic oral contraceptive method. Preferably, the extended contraceptive cycle, including the optional Phase IV composition, is in a range from about 52 to about 62 days, more preferably about 54 to about 58 days, even more preferably about 55 to about 57 days and most preferably about 56 days.

Yet another embodiment of this invention is directed to a multiphase combination and contraceptive kit comprising a package containing: (a) about 7 to about 14 daily dosages of a Phase I composition containing a progestogen in an amount equivalent to about 0.3 to about 1.5 mg norethindrone acetate and an estrogen in an amount equivalent to about 5 to about 15 mcg of ethinyl estradiol; (b) about 14 to about 22 daily dosages of a Phase II composition containing a progestogen in an amount equivalent to about 0.3 to about 1.5 mg of norethindrone acetate and an estrogen in an amount equivalent to about 10 to about 25 mcg of ethinyl estradiol; (c) about 20 to about 31 daily dosages of a Phase III composition containing a progestogen in an amount equivalent to about 0.3 to about 1.5 mg of norethindrone acetate and an estrogen in an amount equivalent to about 15 to about 35 mcg of ethinyl estradiol; and (d) optionally, but preferably, about 2 to about 8 daily dosages of a Phase IV composition containing: (i) an estrogen in an amount equivalent to about 5 to about 20 mcg of ethinyl estradiol, or (ii) a placebo or a non-steroidal component, or (iii) a combination of (i) and (ii), wherein the ethinyl estradiol equivalent amount of estrogen in each of the successive Phases II and III is at least 5 mcg greater than the ethinyl estradiol equivalent amount of estrogen in the immediately-preceding phase. The Phase IV composition is substantially free of progestogen, i.e., there is no therapeutically effective amount present.

The kit is designed for extended cycle use. The kit preferably contains about 7 to about 14 dosages of the Phase I composition; about 14 to about 22 dosages of the Phase II composition; about 20 to about 31 dosages of the Phase III composition, along with about 2 to about 8 dosages of the Phase IV composition.

An advantage of the present invention is that it decreases the number of withdrawal bleeds by about 50%, to about 6 to 7 per year, while additionally minimizing the amount of breakthrough bleeding common to extended oral contraceptive regimens.

Another advantage of the present invention is that it extends the contraceptive regimen to a more practical two-month period, thereby avoiding much of the irregular bleeding commonly associated with three-cycle extended regimens.

Yet another advantage of the present invention is the option it provides for varying the composition in the final fourth phase to comprise either a lower dose of estrogen, a placebo alone, or some combination of the two, depending on the individual needs of a female of child bearing age using the method as described herein.

DETAILED DESCRIPTION OF THE INVENTION

For the purposes of this invention, the designation "mcg" refers to micrograms and "mg" to milligrams.

By practicing the multiphasic contraceptive method disclosed herein, a user advantageously improves control of withdrawal bleeding, sometimes called menstrual bleeding, along with reducing the number of such withdrawal bleeds to between 6 and 7 per year, while taking the estrogenic/progestogenic contraceptive compositions of the invention.

A notable feature of the invention is that the amount of estrogen administered in each of the successive Phase II and III compositions is greater than the amount of estrogen administered in the immediately-preceding phase compositions, during the first three phases. Moreover, in the fourth phase (Phase IV), the amount of estrogen is then reduced from the immediately-preceding phase (Phase III) by at least the equivalent of 5 mcg of ethinyl estradiol, preferably at least about 10 mcg, and most preferably at least about 15 mcg. In one particularly preferred embodiment the amount of ethinyl estradiol in the successive Phase II and III compositions is at least about 5 mcg greater, preferably at least about 10 mcg greater, than the amount of ethinyl estradiol in the immediately-preceding phase composition.

In one particularly preferred embodiment the amount of estrogen in Phase I is equivalent to about 10 mcg of ethinyl estradiol, the amount of estrogen in Phase II is equivalent to about 20 mcg of ethinyl estradiol, the amount of estrogen in Phase III is equivalent to about 30 mcg of ethinyl estradiol, and the amount of estrogen in Phase IV is equivalent to about 15 mcg of ethinyl estradiol. In yet another particularly preferred embodiment the amount of estrogen in Phase I is equivalent to about 10 mcg of ethinyl estradiol, the amount of estrogen in Phase II is equivalent to about 20 mcg of ethinyl estradiol, and the amount of estrogen in Phase III is equivalent to about 30 mcg of ethinyl estradiol, with no estrogen administered in Phase IV.

The progestogen may be selected, for example, from the group consisting of norethindrone acetate, drospirenone, trimegestone, norethindrone, levonorgestrel, desogestrel, 3-ketodesogestrel, gestodene and the like. Other exemplary progestogens include demegestone, dydrogesterone, medrogestone, medroxy progesterone and esters thereof. The most preferred progestogen is norethindrone acetate. The estrogen may be selected, for example, from the group consisting of ethinyl estradiol, 17-β-estradiol, estradiol acetate, conjugated estrogens, mestranol, estrone and esters prodrugs and/or salts thereof. An exemplary ester is estradiol acetate. The most preferred estrogen is ethinyl estradiol. The amount of progestogen and estrogen employed in each phase will be that amount which is equivalent in potency to the ranges of norethindrone acetate and ethinyl estradiol, respectively, that are set forth herein. Determination of equivalent potency is well understood and readily accomplished by those of ordinary skill in the art.

In the female body, the blood-rich mucous membrane lining the uterus, known as the endometrium, adapts to varying levels of estrogen in the body. Much of the bleeding associated with most conventional oral contraceptives is believed to result from over-stimulation with exogenous estrogen early in the cycle. Without wishing to be bound by theory, it is believed that by cycling the amount of estrogen so as to deliver a small dosage at the start of treatment followed by a gradual, progressive increase to higher dosage levels, the endometrium is supported until the estrogen is withdrawn at the end of treatment (e.g., decreasing the amount of estrogen in Phase IV to levels similar to Phase I or lower).

By stimulating the endometrium with exogenous estrogen over a range of about 50 to about 60 days through a step-wise increase in dosage amount so as to avoid premature over-stimulation, it is believed that the integrity of the endometrium may be maintained at an adequate state of at least about 3 to 5 mm thickness, thereby reducing the undesirable incidence of breakthrough bleeding. When able to maintain the integrity of her endometrium over about a two-month period, the female may in turn better control discharge bleeding and extend her cycle. Gradually increasing the dose of estrogens until withdrawal prevents the endometrium from becoming acclimated to a constant estrogen dose which, together with extending the oral contraceptive therapy over about two cycles, lowers the number of withdrawal bleeds to about six per year. It is believed, again without being bound by theory, that this up and down regulation of the estrogen receptors results in the support of the endometrium and lowering of breakthrough bleeding.

The inventive multiphasic method of contraception sequentially administers, to a female of child bearing age: (a) a Phase I composition containing a progestogen in an amount equivalent to about 0.3 to about 1.5 mg norethindrone acetate and an estrogen in an amount equivalent to about 5 to about 15 mcg of ethinyl estradiol for about 7 to about 14 days; (b) a Phase II composition containing a progestogen in an amount equivalent to about 0.3 to about 1.5 mg of norethindrone acetate and an estrogen in an amount equivalent to about 10 to about 25 mcg of ethinyl estradiol for about 14 to about 22 days; (c) a Phase III composition containing a progestogen in an amount equivalent to about 0.3 to about 1.5 mg of norethindrone acetate and an estrogen in an amount equivalent to about 15 to about 35 mcg of ethinyl estradiol for about 20 to about 31 days; and (d) an optional, but preferable Phase IV composition containing: (i) an estrogen in an amount equivalent to about S to about 20 mcg of ethinyl estradiol, or (ii) a placebo or a non-steroidal component, or (iii) a combination of (i) and (ii), for about 2 to about 8 days, wherein the ethinyl estradiol equivalent amount of estrogen in each of the successive Phases II and III is at least 5 mcg greater than the ethinyl estradiol equivalent amount of estrogen in the immediately-preceding phase.

The regimen is practiced in an extended cycle manner. Phase I is administered for about 7 to about 14 days, Phase II is administered for about 14 to about 22 days, Phase III is administered for about 20 to about 31 days, and, if employed, Phase IV is administered for about 2 to about 8 days. It is essential that the phases succeed each other in increasing order (i.e., I, II, III, and IV). Preferably, this may be continued over a period of about 52 days to about 62 days, more preferably about 54 to about 58 days, even more preferably for about 55 to about 57 days, most preferably for about 56 days. When the user desires to discontinue the regimen, and experience a discharge bleeding, she will either begin administering the Phase IV composition or go pill free for a period of about 2 to about 8 days, preferably about 4 to about 8 days. By practicing this regimen, the user may reduce the number of menstrual cycles she will have to as little as six per year.

Under the present invention, the Phase IV composition may constitute a final phase of the extended cycle during which estrogen is administered at a lowered dosage (e.g., at least the amount of estrogen equivalent to 5 μg of ethinyl estradiol less than Phase III estrogen dosage) or, alternatively, may serve as a cleansing period. In this phase, a placebo or a non-steroid component may optionally be administered.

Within Phase IV, three distinct treatment options are available. As a final phase of the extended cycle, the amount of estrogen may be lowered to an amount equivalent to about 5 to about 20 mcg ethinyl estradiol for about 2 to about 4 days, followed by a placebo for about 2 to about 4 days. Alternatively, the amount of estrogen may be equivalent to about 5 to about 20 mcg ethinyl estradiol throughout the entire duration of Phase IV from about 2 to about 8 days, without any placebo. As a third option there may be no estrogen administered during Phase IV with only the placebo taken for about 2 to about 8 days.

In one preferred embodiment, the amount of estrogen in the Phase IV composition is equivalent to about 15 mcg of ethinyl estradiol, administered over a period of about 2 to about 4 days, along with a placebo administered for any of the days during Phase IV that the estrogen is not administered.

In another preferred embodiment, the amount of estrogen in the Phase IV composition is equivalent to about 15 mcg of ethinyl estradiol, administered over a period of about 2 to about 8 days.

In still another preferred embodiment, an optional Phase IV composition of a placebo alone is administered over a period of about 2 to about 8 days, with no estrogen equivalent.

In a particularly preferred embodiment, the placebo in the Phase IV composition is a non-steroidal component comprising an iron supplement. Suitable iron supplements include, for example, ferrous fumarate, ferrous sulfate, ferrous gluconate, iron polysaccharides, and mixtures thereof. The preferred iron supplement is ferrous fumarate.

Preferably, the iron supplement is equivalent to not more than about 75 mg ferrous fumarate.

As noted previously, it is essential that the method of this invention be practiced by administration of the compositions in a numeric sequence with the Phase I composition administered first, the Phase II composition administered second, etc. If packaging and/or other requirements dictate, the method and kit described herein can be employed as part of a larger scheme for contraception or treatment of gynecological disorders. While the sequence in which Applicant's combinations are administered is important to their operation, it should be kept in mind that variations in timing and dosage can be tolerated when medical considerations so dictate.

Although ethinyl estradiol is the estrogenic compound exemplified in this invention, it should be understood that other estrogenic compounds may be substituted as long as the equivalent amount of estrogen is administered.

Similarly, norethindrone acetate is the progestogenic compound exemplified in this invention.

The compositions employed in accordance with the invention in Phases I through IV will more preferably have the administration times and drug contents set forth in Table 1, when a four-phase system is used. This table sets forth relevant values for one of Applicant's preferred embodiments, or configurations, for administration of the system to females.

TABLE 1

| | Day | | | | | | |
|---|---|---|---|---|---|---|---|
| | 1 | 2 | 3 | 4 | 5 | 6 | 7 |
| Composition | A | A | A | A | A | A | A |
| | Day | | | | | | |
| | 8 | 9 | 10 | 11 | 12 | 13 | 14 |
| Composition | A | A | A | B | B | B | B |
| | Day | | | | | | |
| | 15 | 16 | 17 | 18 | 19 | 20 | 21 |
| Composition | B | B | B | B | B | B | B |
| | Day | | | | | | |
| | 22 | 23 | 24 | 25 | 26 | 27 | 28 |
| Composition | B | B | B | B | B | B | B |
| | Day | | | | | | |
| | 29 | 30 | 31 | 32 | 33 | 34 | 35 |
| Composition | C | C | C | C | C | C | C |
| | Day | | | | | | |
| | 36 | 37 | 38 | 39 | 40 | 41 | 42 |
| Composition | C | C | C | C | C | C | C |
| | Day | | | | | | |
| | 43 | 44 | 45 | 46 | 47 | 48 | 49 |
| Composition | C | C | C | C | C | C | C |
| | Day | | | | | | |
| | 50 | 51 | 52 | 53 | 54 | 55 | 56 |
| Composition | C | C | C | E | E | P | P |

Day 1 is first day of bleeding.
A = 1.0 milligrams Norethindrone Acetate and 10 micrograms Ethinyl Estradiol
B = 1.0 milligrams Norethindrone Acetate and 20 micrograms Ethinyl Estradiol
C = 1.0 milligrams Norethindrone Acetate and 30 micrograms Ethinyl Estradiol
E = 15 micrograms Ethinyl Estradiol
P = Placebo In another embodiment of Table I the ethinyl estradiol in A is 5 micrograms, the ethinyl estradiol in B is 10 micrograms, the ethinyl estradiol in C is 15 micrograms and the ethinyl estradiol in E is 5 micrograms.

It should be noted that this table is presented for illustrative purposes only. For example, the cycles described in Table I could be modified as, for instance, by substituting only a placebo across all four days of Phase IV without any estrogen. The substitution of functionally equivalent amounts and kinds of reagent(s) in these schemes is contemplated. For example, the use of sugar or other placebo in place of all or part of the ferrous fumarate is envisioned.

The compositions used in this invention are administered using a suitable daily dosage form, most preferably an oral dosage form. Tablets, pills, capsules and caplets are exemplary dosage forms. In addition, the use of other conventional additives, e.g., fillers, colorants, polymeric binders, and the like is also contemplated. In general any pharmaceutically-acceptable additive which does not interfere with the function of the active components can be used in one or more of the compositions.

Suitable carriers with which the compositions can be administered include lactose, starch, cellulose derivatives and the like used in suitable amounts. Lactose is a preferred carrier. Mixtures of carriers are operable.

The terms "method" and "kit" are used herein to encompass any drug delivery systems via the use of which the 4-phase scheme outlined above can be effectively administered to human females. Combinations of various dosage forms are operable.

The multiphase combination and contraceptive kit of this invention is a package containing the daily dosages of Phase I, II and III compositions, and optionally, but preferably Phase IV compositions, for practicing the method of this invention. Various types of packages for holding contraceptives are well known and it is contemplated that any such packaging may be used or altered for use in the practice of the present invention. For example, an extended cycle package of the present invention would preferably include about 7 to about 14 dosages of the Phase I composition; about 14 to about 22 dosages of the Phase II composition; and about 20 to about 31 dosages of the Phase III composition. A preferred embodiment of the extended cycle package may also include about 2 to about 8 dosages of the Phase IV composition. In another embodiment, the package may include about 2 to about 8 Phase IV dosages of both the estrogen in an amount equivalent to about 5 to about 20 mcg of ethinyl estradiol, as well as the placebo or non-steroid component.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

What is claimed is:

1. A multiphasic method of contraception comprising the steps of sequentially administering to a female of child bearing age:
    (a) a Phase I composition containing a progestogen in an amount equivalent to about 0.3 to about 1.5 mg norethindrone acetate and an estrogen in an amount equivalent to about 5 to about 15 mcg of ethinyl estradiol for about 7 to about 14 days, wherein the Phase I composition is the first composition used by the female of child bearing age in the method of contraception;
    (b) a Phase II composition containing a progestogen in an amount equivalent to about 0.3 to about 1.5 mg of norethindrone acetate and an estrogen in an amount equivalent to about 10 to about 25 mcg of ethinyl estradiol for about 14 to about 22 days;
    (c) a Phase III composition containing a progestogen in an amount equivalent to about 0.3 to about 1.5 mg of norethindrone acetate and an estrogen in an amount equivalent to about 15 to about 35 mcg of ethinyl estradiol for about 20 to about 31 days; and
    (d) a Phase IV composition containing:
        i. an estrogen in an amount equivalent to about 5 to about 20 mcg of ethinyl estradiol, or
        ii. a placebo or a non-steroidal component, or
        iii. a combination of i. and ii.,
    for about 2 to about 8 days,
    wherein the ethinyl estradiol equivalent amount of estrogen in each of the successive Phases II and III is at least 5 mcg greater than the ethinyl estradiol equivalent amount of estrogen in the immediately-preceding phase;

and the sequential administration of the Phase I, II, III and IV compositions is continued from 54 to 58 days to provide an extended contraceptive cycle.

2. The method according to claim 1, wherein the Phase I composition is administered for 10 days, the Phase II composition is administered for 18 days, the Phase III composition is administered for 24 days, and the Phase IV composition is administered for 4 days.

3. The method according to claim 1, wherein the Phase IV composition comprises 4 days of the placebo or non-steroidal component.

4. The method according to claim 1, wherein the Phase IV composition comprises 4 days of an estrogen in an amount equivalent to about 15 mcg of ethinyl estradiol.

5. The method according to claim 1, wherein the Phase IV composition comprises 2 days of an estrogen in an amount equivalent to about 15 mcg of ethinyl estradiol and 2 days of the placebo or non-steroidal component.

6. The method of claim 1, wherein said non-steroidal composition comprises ferrous fumarate.

7. The method according to claim 1, wherein the amount of progestogen in the Phase I, II and III compositions is maintained constant.

8. The method according to claim 1, wherein the norethindrone acetate equivalent amount of progestogen in the Phase I, II and III compositions is about 1 mg of norethindrone acetate.

9. The method according to claim 1, wherein the ethinyl estradiol equivalent amount of estrogen in the Phase I composition is about 10 mcg of ethinyl estradiol, the ethinyl estradiol equivalent amount of estrogen in the Phase II composition is about 20 mcg of ethinyl estradiol, the ethinyl estradiol equivalent amount of estrogen in the Phase III composition is about 30 mcg of ethinyl estradiol, and the ethinyl estradiol equivalent amount of estrogen in the Phase IV composition is about 15 mcg ethinyl estradiol.

10. The method according to claim 1, wherein the ethinyl estradiol equivalent amount of estrogen in the Phase I composition is about 10 mcg of ethinyl estradiol, the ethinyl estradiol equivalent amount of estrogen in the Phase II composition is about 20 mcg of ethinyl estradiol, and the ethinyl estradiol equivalent amount of estrogen in the Phase III composition is about 30 mcg of ethinyl estradiol.

11. A multiphasic method of contraception comprising the steps of sequentially administering to a female of child bearing age:
(a) a Phase I composition containing a progestogen in an amount equivalent to 1.0 mg norethindrone acetate and an estrogen in an amount equivalent to 10 mcg of ethinyl estradiol for 10 days, wherein the Phase I composition is the first composition used by the female of child bearing age in the method of contraception;
(b) a Phase II composition containing a progestogen in an amount equivalent to 1.0 mg of norethindrone acetate and an estrogen in an amount equivalent to 20 mcg of ethinyl estradiol for 18 days;
(c) a Phase III composition containing a progestogen in an amount equivalent to 1.0 mg of norethindrone acetate and an estrogen in an amount equivalent to 30 mcg of ethinyl estradiol for 24 days; and
(d) a Phase IV composition containing:
  i. an estrogen in an amount equivalent to about 5 to about 20 mcg of ethinyl estradiol, or
  ii. a placebo or a non-steroidal component, or
  iii. a combination of i. and ii.,
for 4 days.

12. The method according to claim 11, wherein the Phase IV composition comprises an estrogen in an amount equivalent to 15 mcg of ethinyl estradiol for 4 days.

13. The method according to claim 11, wherein the Phase IV composition comprises a placebo or non-steroidal component for 4 days.

14. The method according to claim 11, wherein the Phase IV composition comprises an estrogen in an amount equivalent to 15 mcg of ethinyl estradiol for 2 days, followed by a placebo or non-steroidal component for 2 days.

15. A multiphase combination and contraceptive kit comprising a package containing:
(a) about 7 to about 14 daily dosages of a Phase I composition containing a progestogen in an amount equivalent to about 0.3 to about 1.5 mg norethindrone acetate and an estrogen in an amount equivalent to about 5 to about 15 mcg of ethinyl estradiol;
(b) about 14 to about 22 daily dosages of a Phase II composition containing a progestogen in an amount equivalent to about 0.3 to about 1.5 mg of norethindrone acetate and an estrogen in an amount equivalent to about 10 to about 25 mcg of ethinyl estradiol;
(c) about 20 to about 31 daily dosages of a Phase III composition containing a progestogen in an amount equivalent to about 0.3 to about 1.5 mg of norethindrone acetate and an estrogen in an amount equivalent to about 15 to about 35 mcg of ethinyl estradiol; and
(d) about 2 to about 8 daily dosages of a Phase IV composition containing:
  i. an estrogen in an amount equivalent to about 5 to about 20 mcg of ethinyl estradiol, or
  ii. a placebo or a non-steroidal component, or
  iii. a combination of i. and ii.,
wherein the ethinyl estradiol equivalent amount of estrogen in each of the successive Phases II and III is at least 5 mcg greater than the ethinyl estradiol equivalent amount of estrogen in the immediately-preceding phase, wherein the kit instructs a user of the kit that each of the Phase I, II, III and IV dosages must succeed each other in increasing order, and wherein the combined dosages of Phase I, II, III and IV compositions in the kit are from 54 to 58.

16. The kit according to claim 15, wherein the kit contains about 7 to about 14 dosages of the Phase I composition; about 14 to about 22 dosages of the Phase II composition; about 20 to about 31 dosages of the Phase III composition; and about 2 to about 8 dosages of the Phase IV composition.

17. The kit according to claim 15, wherein the progestogen is selected from the group consisting of norethindrone acetate, drospirenone, trimegestone, norethindrone, levonorgestrel, desogestrel, 3-ketodesogestrel, gestodene, demegestone, dydrogesterone, medrogestone, medroxy progesterone, esters and mixtures thereof.

18. The kit according to claim 17, wherein the progestogen is norethindrone acetate.

19. The kit according to claim 15, wherein the estrogen is selected from the group consisting of ethinyl estradiol, 17-β-estradiol, conjugated estrogens, mestranol, estrone, and esters, prodrugs and salts thereof.

20. The kit according to claim 19, wherein the estrogen is ethinyl estradiol.

21. The kit according to claim 15, wherein the norethindrone acetate equivalent amount of progestogen in the Phase I, II and III compositions is about 1 mg of norethindrone acetate.

22. The kit according to claim 15, wherein the ethinyl estradiol equivalent amount of estrogen in the Phase I composition is about 10 mcg ethinyl estradiol, the ethinyl estradiol equivalent amount of estrogen in the Phase II composition is about 20 mcg of ethinyl estradiol, the ethinyl estradiol equivalent amount of estrogen in the Phase III composition is about 30 mcg of ethinyl estradiol, and the Phase IV composition contains about 75 mg of ferrous fumarate.

23. The kit according to claim 22, wherein the estrogen and progestogen in the Phase I, II and III compositions are, respectively, ethinyl estradiol and norethindrone acetate.

24. The kit according to claim 15, wherein the ethinyl estradiol equivalent amount of estrogen in the Phase I composition is about 10 mcg ethinyl estradiol, the ethinyl estradiol equivalent amount of estrogen in the Phase II composition is about 20 mcg of ethinyl estradiol, the ethinyl estradiol equivalent amount of estrogen in the Phase III composition is about 30 mcg of ethinyl estradiol, and the Phase IV composition is about 15 mcg of ethinyl estradiol.

25. The kit according to claim 24, wherein the estrogen and progestogen in the Phase I, II and III compositions are, respectively, ethinyl estradiol and norethindrone acetate.

* * * * *